United States Patent [19]

Peeters

[11] 4,447,609

[45] May 8, 1984

[54] METHOD OF PREPARING 2-ALKOXY-4-AMINOPYRIMIDINES

[75] Inventor: Hermann Peeters, Niederkassel, Fed. Rep. of Germany

[73] Assignee: Dynamit Nobel AG, Troisdorf, Fed. Rep. of Germany

[21] Appl. No.: 358,973

[22] Filed: Mar. 17, 1982

[30] Foreign Application Priority Data

Mar. 25, 1981 [DE] Fed. Rep. of Germany ....... 3111613

[51] Int. Cl.$^3$ ............................................. C07D 239/24
[52] U.S. Cl. ..................................... 544/317; 424/251

[58] Field of Search .................. 544/316, 317, 315; 424/253

[56] References Cited

U.S. PATENT DOCUMENTS 4,188,484 2/1980 Scolastico et al. ................... 544/317

*Primary Examiner*—Nicholas S. Rizzo
*Attorney, Agent, or Firm*—Felfe & Lynch

[57] ABSTRACT

2-Alkoxy-4-aminopyrimidines, having if desired a substituent in position 5, are prepared from 4-amino-2-carboxymethylthiopyrimidines by conversion with alcohols in the presence of bases.

16 Claims, No Drawings

METHOD OF PREPARING 2-ALKOXY-4-AMINOPYRIMIDINES

This invention relates to a process for preparing 2-alkoxy-4-aminopyrimidine compounds.

The synthesis of 4-amino-2-alkoxypyrimidines has hitherto been expensive. The unsubstituted 4-amino-2-alkoxypyrimidine is formed of 2,4-dichloropyrimidine by transposition with ammonia and further reaction of the 4-amino-2-chloropyrimidine with alkali methylate, whereupon an isomer mixture is formed which can be separated only at great expense (J. Amer. Chem. Soc. 52 (1930) 1152; C.A. 52, 6360 b), and by the hydrogenation of the difficultly obtainable 4-amino-6-chloro-2-alkoxypyrimidine (Monatsheft Chem. 94 (1963) 1178), or by reaction of 2,4-dimethoxypyrimidine with sodium amide in liquid ammonia (C.A. 58, 5460). The 4-amino-2-methoxypyrimidine substituted in the 5th position by the hydroxymethyl group has been prepared only by the reduction of the difficultly obtainable 4-amino-5-ethoxycarbonyl-2-methoxy-pyrimidine with lithium aluminum hydride (J. Org. Chem. 27 (1962) 3614).

THE INVENTION

The object of the present invention was to synthesize 2-alkoxypyrimidines in a high yield by a simple reaction from easily available and inexpensive starting products. Expensive and complex processes, such as isomer separation, were to be avoided.

The subject matter of the invention is a method of preparing 2-alkoxy-4-aminopyrimidines of the formula

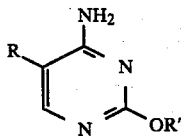
    1 wherein R represents a hydrogen atom, straight-chain, branched or cyclic alkyl moieties of 1 to 20 carbon atoms, straight-chain or branched moieties $(CH_2)_nCN$, $(CH_2)_n$—$COOR''$, $(CH_2)_n$—$NH_2$, $(CH_2)_nOR''$, $(CH_2)_n$—Cyc, Cyc representing an isocyclic or heterocyclic ring of a mono- or polycyclic structure, which can have substituents on the ring if desired, R" representing alkyl moieities of 1 to 15 carbon atoms or moieties of univalent phenols and $n=1$ to 5, and R' representing straight-chain, branched or cyclic alkyl moieties of 1 to 10 carbon atoms or $(CH_2)_n$Cyc, wherein n and Cyc have the meaning given above, which is characterized in that a 4-amino-2-carboxymethylthiopyrimidine of the formula

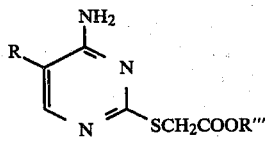
    2 wherein R has the same meaning as in formula 1 and R''' represents hydrogen or a straight-chain, branched or cyclic alkyl moiety of 1 to 10 carbon atoms, is reacted, in the presence of a base, with an alcohol of the formula

HOR'    3.

wherein R' has the same meaning as in formula 1.

The process delivers the products in high purity and yield.

The 4-amino-2-carboxymethylthiopyrimidines of formula 2 are easily obtained by the reaction of 4-amino-2-mercaptopyrimidines with chloroacetic acid or chloroacetic acid esters (J. Biol. Chem. 177 (1949) 357).

For the practice of the present invention, a 4-amino-2-carboxymethylthiopyrimidine (formula 2), in which the group —COOH is used very preferentially, and also preferentially —$COOCH_3$ and $COOC_2H_5$, as the carboxy group, is reacted with an alcohol in the presence of a base.

The alcohol is generally used in an excess with respect to the 4-amino-2-carboxymethylthiopyrimidine and serves as a solvent or dispersant; the minimum amount of alcohol is generally determined by the stirrability of the reaction solution, but the amount can be reduced, if desired, to about 2 moles per mole of 4-amino-2-carboxymethylthio compound of formula 2. The concentration of the reaction solution should be as great as possible.

Preferred alcohols are methanol, ethanol, propanol and butanol.

The alcoholate corresponding to the alcohol is preferred as the base, advantageously sodium alcoholate or potassium alcoholate, but other alcoholates can be used, such as alkaline earth alcoholates for example. Other suitable bases are especially the alkali hydroxides or, in some cases, alkaline earth hydroxides, alkaline earth oxides, or salts of weak acids, such as carbonates for example. The amount of alcohol will be from 2 to 20, preferably 2 to 10 moles per mole of 4-amino-2-carboxymethylthiopyrimidine and 1 to 20, preferably 2 to 10, moles per mole of 4-amino-2-alkoxycarbonylmethylthiopyrimidine.

The reaction requires elevated temperatures. The preferred temperature is the boiling point of the solvent, although even higher temperatures of up to about 150° C. are possible under a slight excess pressure. The reaction time amounts generally to 1 to 10 hours.

The working up of the reaction product varies depending on the properties of the product. For example, the poorly water-soluble 4-amino-2-methoxypyrimidine can be precipitated by the addition of water after the reaction has ended and the methanol has been distilled out, and can be separated from the water-soluble components.

4-Amino-2-alkoxypyrimidines are starting products, for example for pharmaceutically active sulfonamides and for cytosine and cytosine derivatives.

EXAMPLES

Example 1

37 g (0.2 mol) of 4-amino-2-carboxymethylthiopyrimidine and 108 g of a 30% methanolic sodium methylate solution (0.6 mol of sodium methylate) are mixed at room temperature and refluxed for 3 hours. After withdrawal of the solvent 150 ml of water is added and the mixture is stirred for about one hour at 50°–60° C. The solution is cooled to 20° C., and the solid matter is removed, washed with water and vacuum dried.

Yield: 22.3 g (89.2% of the theory) 4-amino-2-methoxypyrimidine. Melting point: 166°–168° C.

Example 2

9.3 g (0.05 mol) of 4-amino-2-carboxymethylthiopyrimidine is refluxed with 6.6 g (0.165 mol) of sodium hydroxide in 40 ml of methanol for 3 hours. After working up as in Example 1, 4.7 g (75.2% of the theory) of 4-amino-2-methoxypyrimidine is obtained.

Example 3

9.3 g (0.05 mol) of 4-amino-2-carboxymethylthiopyrimidine is refluxed for 3 hours in 120 g of a 17% ethanolic sodium ethylate solution (0.3 mol of sodium ethylate). The solvent is withdrawn the residue dissolved in 50 ml of water and extracted with ether, and after drying the ether is withdrawn. The residue is recrystallized from a mixture of ether and petroluem ether.

Yield: 4.8 g (69.1% of theory) of 4-amino-2-ethoxypyrimidine. M.P.: 72.76° C.

Example 4

19.9 g (0.1 mol) of 4-amino-methoxycarbonylmethylthiopyrimidine is refluxed for 3 hours in 81 g of a 30% methanolic sodium methylate solution (0.45 mol of sodium methylate). After working up as in Example 1, 9.5 g (76.0% of the theory) of 4-amino-2-methoxypyrimidine is obtained.

Example 5

1.0 g (0.005 mol) of 4-amino-5-methyl-2-carboxymethylthiopyrimidine is refluxed for 3 hours in 7.2 g of a 17% methanolic sodium methylate solution (0.0225 mol). After working up as in Example 3, 0.31 g (44.6% of the theory) of 4-amino-2-methoxy-5-methylpyrimidine is obtained.
M.P.: 103°–107° C.

Example 6

5.5 g (0.02 mol) of 4-amino-5-benzyl-2-carboxymethylthiopyrimidine is refluxed in 28.6 g of methanolic sodium methylate solution for three hours. After working up as in Example 1, 3.1 g (72.1% of the theory) of 4-amino-5-benzyl-2-methoxypyrimidine is obtained.
M.P.: 140°–141° C.

Example 7

42.8 g (0.2 mol) of 4-amino-5-methoxymethyl-2-carboxymethylthiopyrimidine is reacted in the manner described in Example 1, and 4-amino-5-methoxymethyl-2-methoxypyrimidine is obtained in the same yield.

It will be understood that the specification and examples are illustrative but not limitative of the present invention and that other embodiments within the spirit and scope of the invention will suggest themselves to those skilled in the art.

What is claimed is:

1. Process for preparing 2-alkoxy-4-aminopyrimidine compounds of the formula:

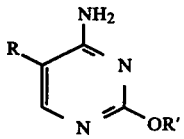

wherein
R is hydrogen, alkyl of from 1 to about 20 carbon atoms, or a straight or branched moiety selected from the group consisting of
$(CH_2)_nCN$
$(CH_2)_n$—COOR'',
$(CH_2)_n$—NH_2,
$(CH_2)_nOR''$, and
benzyl;
R'' is an alkyl moiety of from 1 to about 12 carbon atoms or a univalent phenol moiety;
n is an integer from 1 to 5 and
R' is straight chain or branched alkyl of from 1 to about 10 carbon atoms; by reacting a 4-amino-2-carboxymethyl-thiopyrimidine of the formula:

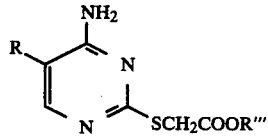

wherein R is defined as above, and R''' is hydrogen or alkyl of from 1 to about 10 carbon atoms
with an excess of alcohol of the formula:

HOR' wherein R' is defined as above,
in the presence of a base having the following formula:

$XOR^4$ wherein X is an alkali or alkaline earth metal and $R^4$ is hydrogen, or an alkyl having from 1 to about 10 carbon atoms, in an amount sufficient to form an alkaline reaction mixture.

2. Process as claimed in claim 1, wherein at least 1 mole of the said alcohol is used per mole of pyrimidine.

3. Process as claimed in claim 1, wherein R is hydrogen.

4. Process as claimed in claim 1, wherein R is alkyl.

5. Process as claimed in claim 1, wherein R is $(CH_2)_nCHN$.

6. Process as claimed in claim 1, wherein R is $(CH_2)_n$—COOR''.

7. Process as claimed in claim 1, wherein R is $(CH_2)_n$—NH_2.

8. Process as claimed in claim 1, wherein R is $(CH_2)_nOR''$.

9. Process as claimed in claim 1, wherein R is $(CH_2)_n$—Cyc.

10. Process as claimed in claim 1, wherein the reaction takes place at approximately the boiling temperature of the solvent.

11. Process as claimed in claim 1, wherein the reaction takes place at an elevated temperature ranging up to 150° C.

12. Process as claimed in claim 1, wherein the molar ratio range of alcohol to 4-amino-2-carboxy methylthiopyrimidine is about 1:1 to 20:1.

13. Process as claimed in claim 1, wherein the molar ratio range of alcohol to 4-amino-2-carboxy methylthiopyrimidine is about 1:1 to 10:1.

14. Process as claimed in claim 1, wherein X is Na+ or K+ and
$R^4$ is hydrogen or alkyl having from 1 to 4 carbon atoms.

15. Process as claimed in claim 1, wherein the molar ratio range of alcohol to 4-amino-2-carboxy methylthiopyrimidine is about 1 to 20:1.

16. A process as claimed in claim 1, wherein R is an unsubstituted benzyl.

* * * * *